United States Patent
Nakamura et al.

(10) Patent No.: US 6,793,669 B2
(45) Date of Patent: Sep. 21, 2004

(54) ACTIVE FORCEPS

(75) Inventors: Yoshihiko Nakamura, Edogawa-ku (JP); Masafumi Okada, Bunkyo-ku (JP); Koichi Watabe, Toride (JP)

(73) Assignee: The University of Tokyo, Tokyo (JP)

( * ) Notice: Subject to any disclaimer, the term of this patent is extended or adjusted under 35 U.S.C. 154(b) by 67 days.

(21) Appl. No.: 10/095,689

(22) Filed: Mar. 13, 2002

(65) Prior Publication Data

US 2003/0028217 A1 Feb. 6, 2003

(30) Foreign Application Priority Data

Jul. 31, 2001 (JP) ........................................ 2001-232240

(51) Int. Cl.[7] .............................................. A61B 17/28
(52) U.S. Cl. ..................................................... 606/205
(58) Field of Search ................................ 606/205, 207, 606/208, 170; 600/106, 117

(56) References Cited

U.S. PATENT DOCUMENTS

| | | | | |
|---|---|---|---|---|
| 5,228,451 A | * | 7/1993 | Bales et al. | 600/564 |
| 5,339,799 A | * | 8/1994 | Kami et al. | 600/117 |
| 5,431,645 A | * | 7/1995 | Smith et al. | 606/1 |
| 5,454,378 A | * | 10/1995 | Palmer et al. | 600/564 |
| 5,722,422 A | * | 3/1998 | Palmer et al. | 600/564 |
| 5,782,748 A | * | 7/1998 | Palmer et al. | 600/104 |

* cited by examiner

Primary Examiner—Kevin T. Truong
Assistant Examiner—Victor X Nguyen
(74) Attorney, Agent, or Firm—Oliff & Berridge, PLC (57) ABSTRACT

Endoscopic surgical operation such as evisceration has been so far hardly achieved by a medical robot, since it requires high power. The present invention provides a downsized high-flexibility active forceps to enable such an operation, without needing a large space for manipulation to target a limited operative area. An active forceps of the present invention comprises: a tip forceps part 4 having, a tip supporting member 2 to support a forceps tip 1 at a center section 2a with a plurality of arms 2b laterally projected therefrom, and a plurality of tip side advancing and retreating members 3 connected at a front end with the plurality of arms respectively oscillatable while connected to one another relatively movable in directions toward front and rear ends; and a forceps bottom part 9 having, a plurality of bottom side advancing and retreating members 6 each integrally coupled to the plurality of tip side advancing and retreating members 3, while connected to one another relatively movable indirections toward front and rear ends to constitute a link mechanism together with the tip side advancing and retreating members 3 and the tip supporting member 2, and a bottom frame 8 provided with forward and backward actuating means 7 for moving relatively to one another the bottom side advancing and retreating members 6 in directions toward front and rear ends.

9 Claims, 6 Drawing Sheets

ACTIVE FORCEPS

BACKGROUND OF THE INVENTION

1. Field of the Invention

The present invention relates to an active forceps used for less invasive surgical operation and more particularly to a downsized high-stiffness active forceps.

2. Related Art

In the prior art, most of the active forceps in master-slave-type robot for less invasive surgical operation (particularly for endoscopic surgical operation) has been wire-driven, since it is relatively easy by driving it with wire to realize a downsized mechanism changing orientation by a driving force transmitted from an actuator positioned at the bottom to the tips of forceps.

However, a wire-driven forceps has been used for endoscopic operations such as suture of blood vessels with no requirements of strong force, since it is difficult to transmit a strong force to the tips of the forceps even with a high driving force of the actuator, due to the poor stiffness and durability of wire likely to be stretched or cut.

When an active forceps is used for evisceration, for example, an actuator with strong driving force efficiently transmitted to forceps tips of high stiffness is required to hold organs at the forceps tips. Therefore, the above conventional wire-driven active forceps have been inappropriate for evisceration.

SUMMARY OF THE INVENTION

An object of the present invention is to provide an active forceps capable of solving the above problem advantageously. An active forceps of the present invention comprises: a forceps tip part having a tip supporting member to support a forceps tip at a center section with a plurality of arms laterally projected therefrom, and a plurality of tip side advancing and retreating members connected at a front end with the plurality of arms respectively oscillatable while connected to one another relatively movable in directions toward front and rear ends; and a forceps bottom part having a plurality of bottom side advancing and retreating members each integrally coupled to the plurality of tip side advancing and retreating members, while connected to one another relatively movable in directions toward front and rear ends to constitute a link mechanism together with the tip side advancing and retreating members and the tip supporting member, and a bottom frame provided with a forward and backward actuating means for moving relatively to one another the bottom side advancing and retreating members toward front and rear ends.

Figure 1A:
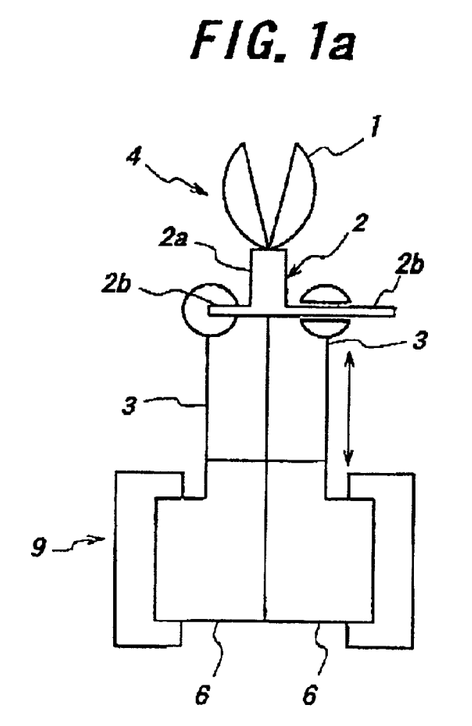
Figure 1B:
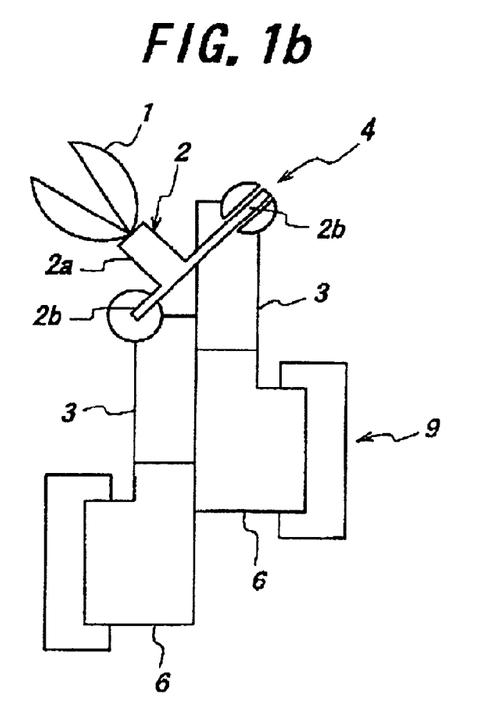

FIG. 1 schematically illustrates the operation of the active forceps according to the present invention having respectively a pair of tip side advancing and retreating members and a pair of bottom side advancing and retreating members. As illustrated, in an active forceps of the present invention, a plurality of bottom side advancing and retreating members 6 constituting a link mechanism together with tip side advancing and retreating members 3 and forceps tip supporting member 2 are moved by actuating means, arranged at an unillustrated bottom frame of forceps bottom 9, from the starting position as shown in FIG. 1(*a*) relatively to one another toward front and rear ends as shown in FIG. 1(*b*). In the drawings, left bottom side advancing and retreating member 6 is fixed, while right bottom side advancing and retreating member 6 is advanced upward. Then, as a result of the relative movement of these bottom side advancing and retreating members 6 toward front and rear ends, a plurality of tip side advancing and retreating members 3 each integrally coupled with those bottom side advancing and retreating members 6, while connected to one another relatively movable toward front and rear ends (up and down as shown in the drawings) are relatively moved toward front and rear ends. In the drawing, left tip side advancing and retreating member 3 stands still, while right tip side advancing and retreating member 3 is advanced upward. Caused by this, forceps tip supporting member 2 at forceps tip part 4 moves a plurality of arms 2*b* laterally projected from center section 2*a* toward front and rear ends of tip side advancing and retreating member 3 to oscillate as a whole (oscillate anti-clockwise in the drawing), thereby changing orientation of forceps tip 1 supported at center section 2*a* (turning from the front facing position to a slanting left position in the drawing). On the other hand, when right bottom side advancing and retreating member 6 is retreated downward, on the contrary to the above, by the above actuating means (not shown), forceps tip 1 turns from the front facing position to a slanting right position.

However, FIG. 1 shows an example of 1-degree-of-freedom oscillation where right tip side advancing and retreating member 3 coupled to right bottom side advancing and retreating member 6 connects arms 2*b* of forceps tip supporting member 2 slidably and oscillatably, while left tip side advancing and retreating member 3 coupled to fixed left bottom side advancing and retreating member 6 connects arms 2*b* of forceps tip supporting member 2 only oscillatably. On the other hand, in the case of oscillation having two degrees of freedom or more with three or more of tip and bottom side advancing and retreating member respectively, a tip side advancing and retreating member coupled to a fixed bottom side advancing and retreating member may also connect arms of a forceps tip supporting member oscillatably as well as slidably, Therefore, in the active forceps according to the present invention, the actuating means can change orientation of a forceps tip by efficiently transmitting a driving force to the forceps tip via the link mechanism, while making the forceps tip more stiff than wire-driven ones, thereby enabling application of the forceps to operations with strong force requirements at the forceps tip, such as evisceration. Moreover, the forceps tip part is mainly provided only with the tip side advancing and retreating members, the tip supporting members, the forceps tip, and connecting members, as needed, integrally coupling those tip side advancing and retreating members and bottom side advancing and retreating members. Therefore, the part of tip side from the forceps bottom part can be easily downsized with a smaller diameter, thereby enabling less invasive surgical operation e.g. in the case of evisceration with strong force requirements at the forceps tip.

Incidentally, in the active forceps according to the present invention, the forceps bottom part may have a rotation actuating means to rotate the bottom frame around a predetermined axis parallel to the direction toward front and rear ends of the bottom side advancing and retreating members together with the forward and backward actuating means and the above bottom side advancing and retreating members. In this case, it rotates the part of tip side from the forceps bottom, to rotate the forceps tip, by rotating the bottom frame around a predetermined axis parallel to the directions of front and rear ends of the bottom side advancing and retreating members together with the forward and backward actuating means and the bottom side advancing and retreating members, thereby highly stiffening the forceps tip, while permitting the part of tip side from the bottom part of the forceps to be downsized with a smaller diameter, with better degrees of freedom in changing orientation of the forceps tip.

Moreover, in the active forceps according to the present invention, the plurality of tip side advancing and retreating members and the plurality of bottom side advancing and retreating members may be fitted into one another slidable toward front and rear ends, while, in an intersecting direction, coupled to one another relatively movable toward front and rear ends by engaging grooves and protrusions. In this case, the plurality of tip side advancing and retreating members and the plurality of bottom side advancing and retreating members are coupled to one another with high stiffness, thereby highly stiffening the forceps tip in a simple construction.

Moreover, in the active forceps according to the present invention, at least either the plurality of tip side advancing and retreating members or the plurality of bottom side advancing and retreating members may be formed of high-silicon stainless steel such as silicolloy (trade name). In this case, a driving force can be transmitted more efficiently, through the affect of the extremely small friction coefficient between high-silicon stainless steel pieces.

Moreover, in the active forceps according to the present invention, the forward and backward actuating means may fix with magnet at the bottom frame one of the plurality of bottom side advancing and retreating members, while removably fitting into the rest of the bottom side advancing and retreating members to advance or retreat the bottom side advancing and retreating members. In this case, the bottom side advancing and retreating members can be easily removed from the forward and backward actuating means together with the part of tip side from the forceps bottom part, making it easy to change, wash, sterilize, etc. such part. In addition, one of the plurality of bottom side advancing and retreating members is fixed at the bottom frame, thereby enabling a smaller number of bottom side advancing and retreating members than the total number thereof to be directly moved by the forward and backward actuating means, to downsize the forceps bottom part in a smaller construction.

BRIEF DESCRIPTION OF THE DRAWINGS

FIGS. 1(*a*) and (*b*) schematically explain the operation of the active forceps according to the present invention having a pair of tip side advancing and retreating members and a pair of bottom side advancing and retreating members, respectively;

FIG. 4(*a*) is a front view of the tip part, with the tip removed and FIG. 4(*b*) is a perspective view of a forceps tip supporting member of the tip part;

FIGS. 6(*a*) and (*b*) explain how to fit the bottom side advancing and retreating members to a forward and backward actuating mechanism of the above forceps bottom.

DESCRIPTION OF PREFERRED EMBODIMENT OF THE INVENTION

Now, a preferred embodiment of the present invention will be explained in detail hereafter referring to drawings. In FIGS. 2 to 6(*a*), (*b*), the same parts as in FIG. 1 are denoted with the same reference numerals or symbols.

Figure 2:
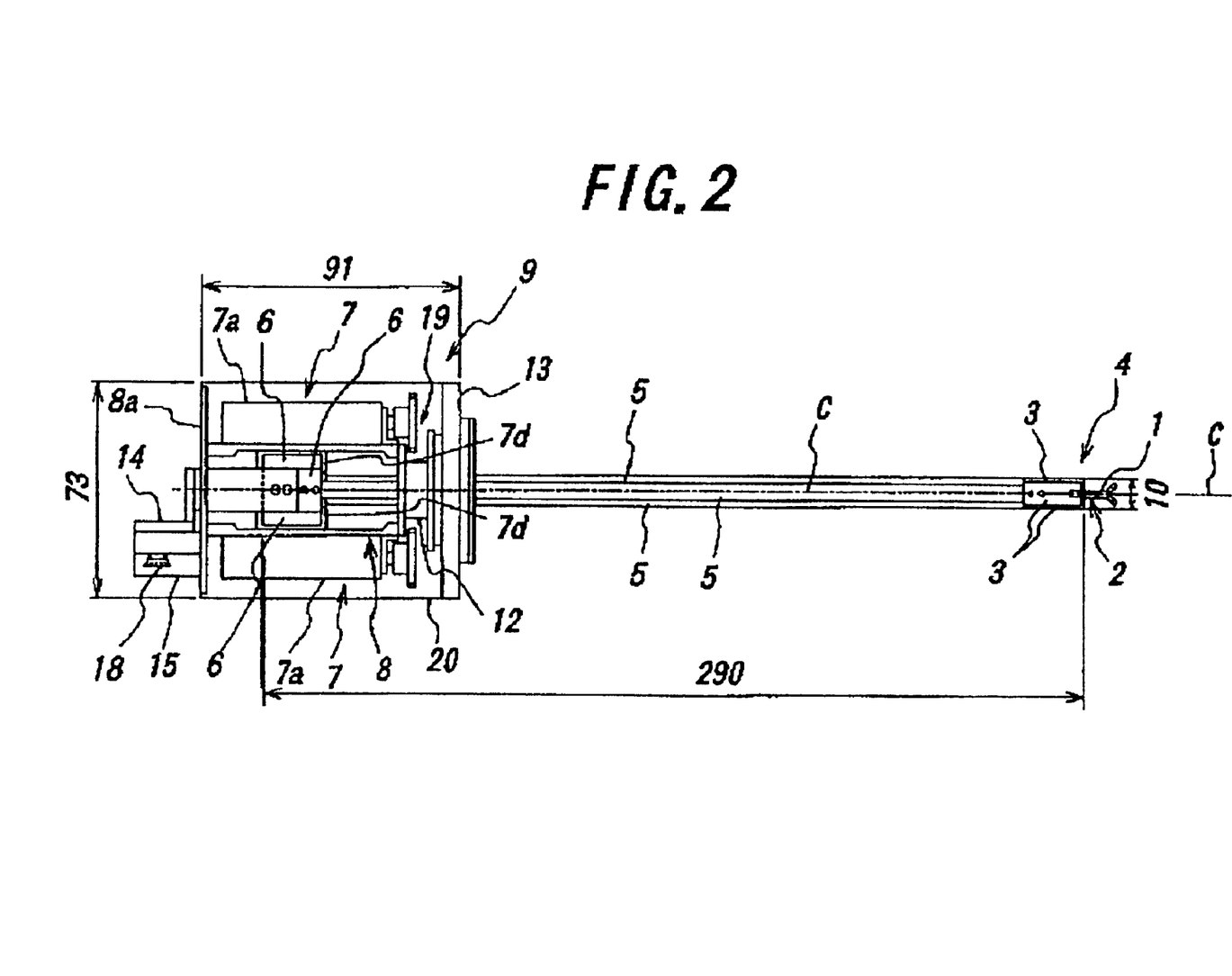
FIG. 2 is a side view of an embodiment of the active forceps according to the present invention.
Figure 3:
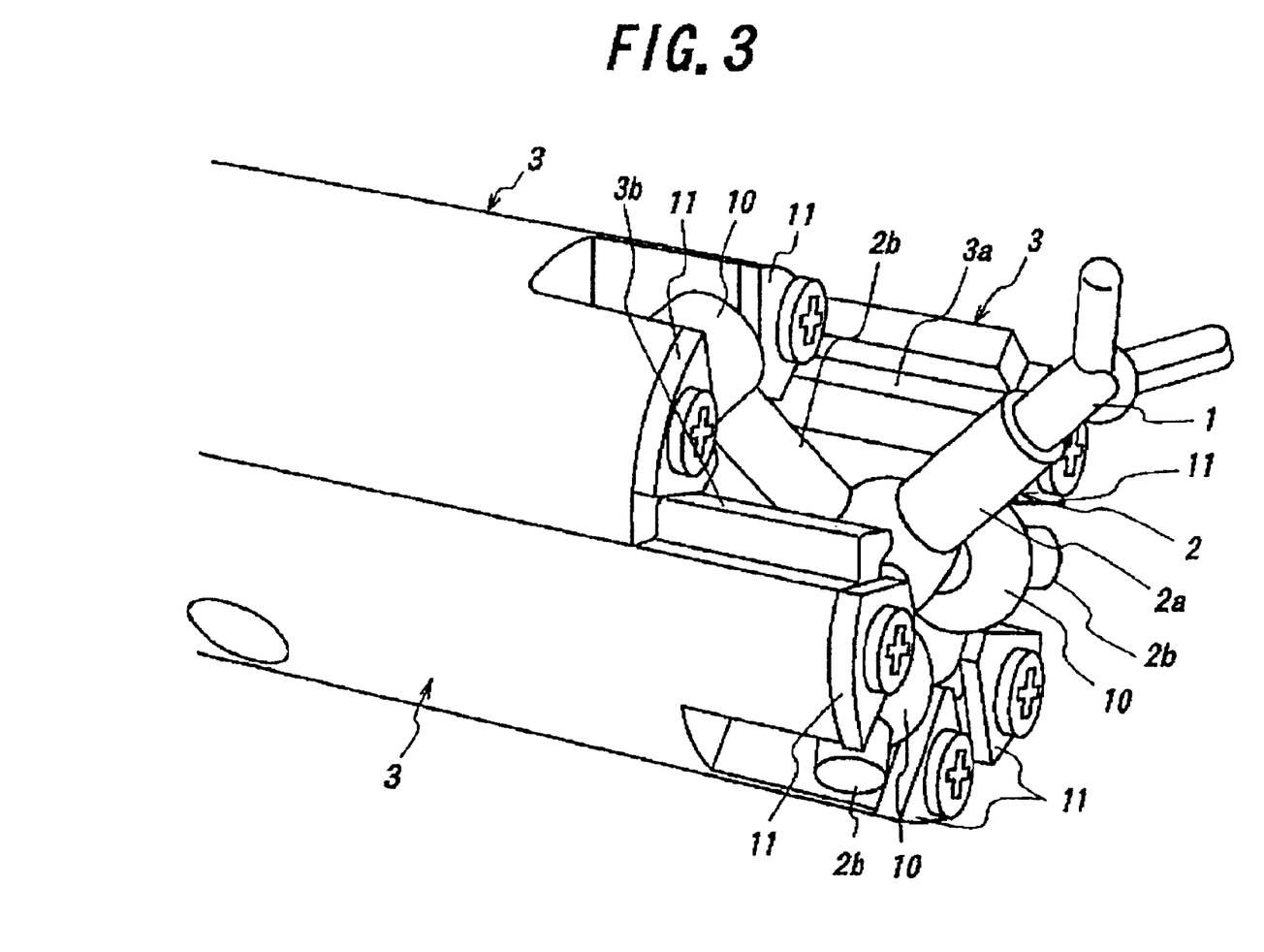
FIG. 3 is a perspective view a of a forceps tip part of active forceps of the above embodiment.
Figure 4A:
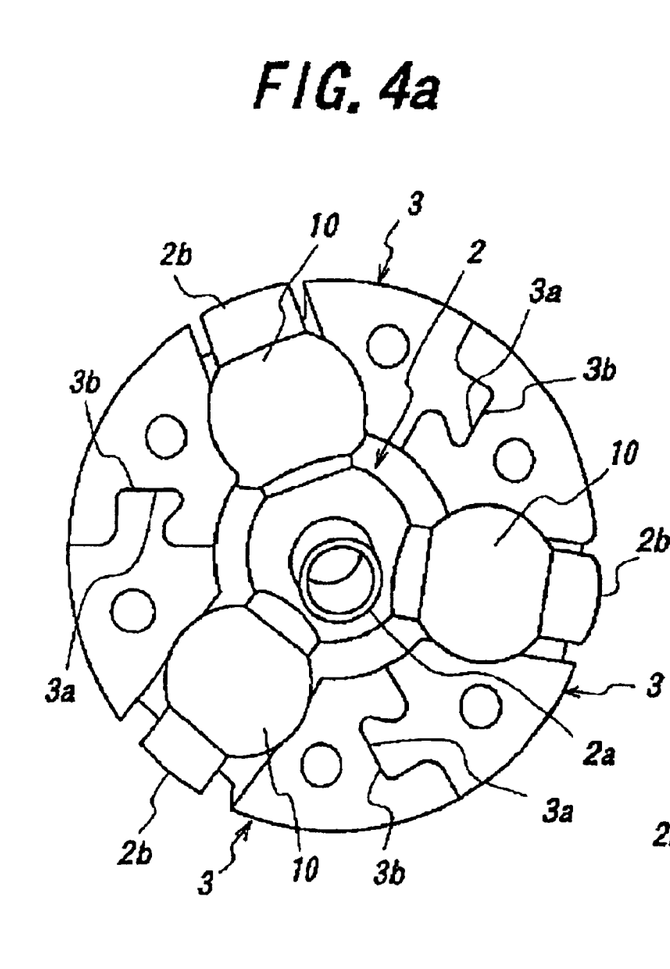
Figure 4B:
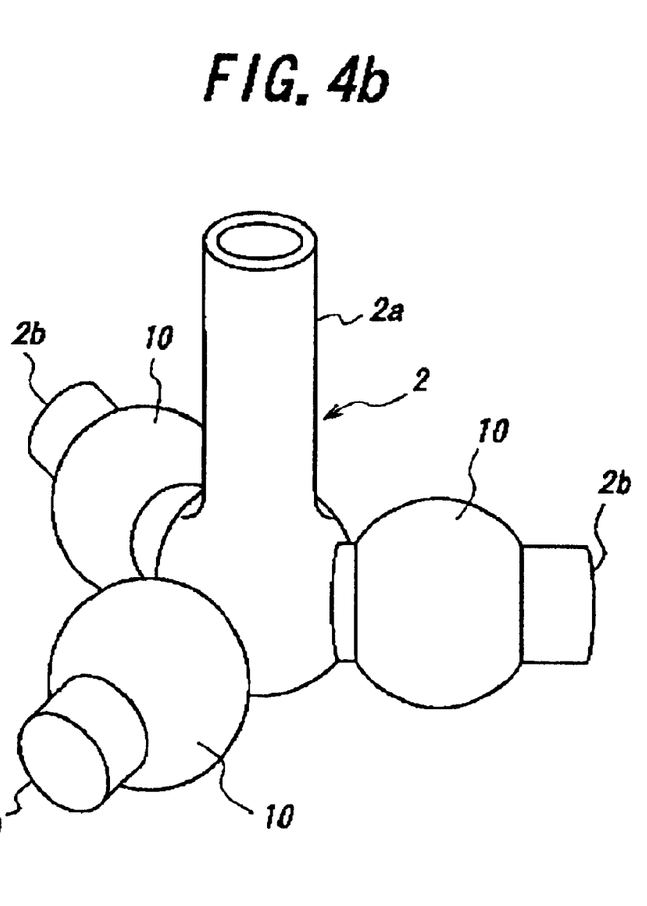

An active forceps of this embodiment comprises a forceps tip part 4 having, as shown in FIGS. 3 and 4, a tip supporting member 2 with a tubular center section 2*a* to support forceps tip 1 opened and closed by manipulation with wire, and three arms 2*b* laterally projected from the center section 2*a*, and having three up side advancing and retreating members 3 connected at a front end oscillatably and slidably with three arms 2*b* of the tip supporting member 2 respectively via ball 10 constituting a ball joint. The three tip side advancing and retreating members 3 here are fitted into one another slidably toward front and rear ends, while, in an intersecting direction, coupled to one another relatively movably to the directions toward front and rear ends by inseparably engaging grooves 3*a* and protrusions 3*b* e.g. of hook-shaped cross section, as shown in FIG. 4(*a*) in this case, extending in the direction of front and rear ends (left and right in FIG. 2 or approximately left and right in FIG. 3).

Incidentally, each ball 10 having pores to insert the respective arms 2*b* of forceps tip supporting member 2, as allowed to advance, retreat and rotate as shown in FIG. 4(*a*), is rotatably supported in a squared groove radially arranged at a tip of each tip side advancing and retreating member 3, slidably abutting a partial spherical surface formed on opposing side walls of the squared groove, while prevented from going out of position by a pair of stopper plates 11 secured by screws to the tip of each tip side advancing and retreating member 3, to constitute a ball joint.

Figure 5:
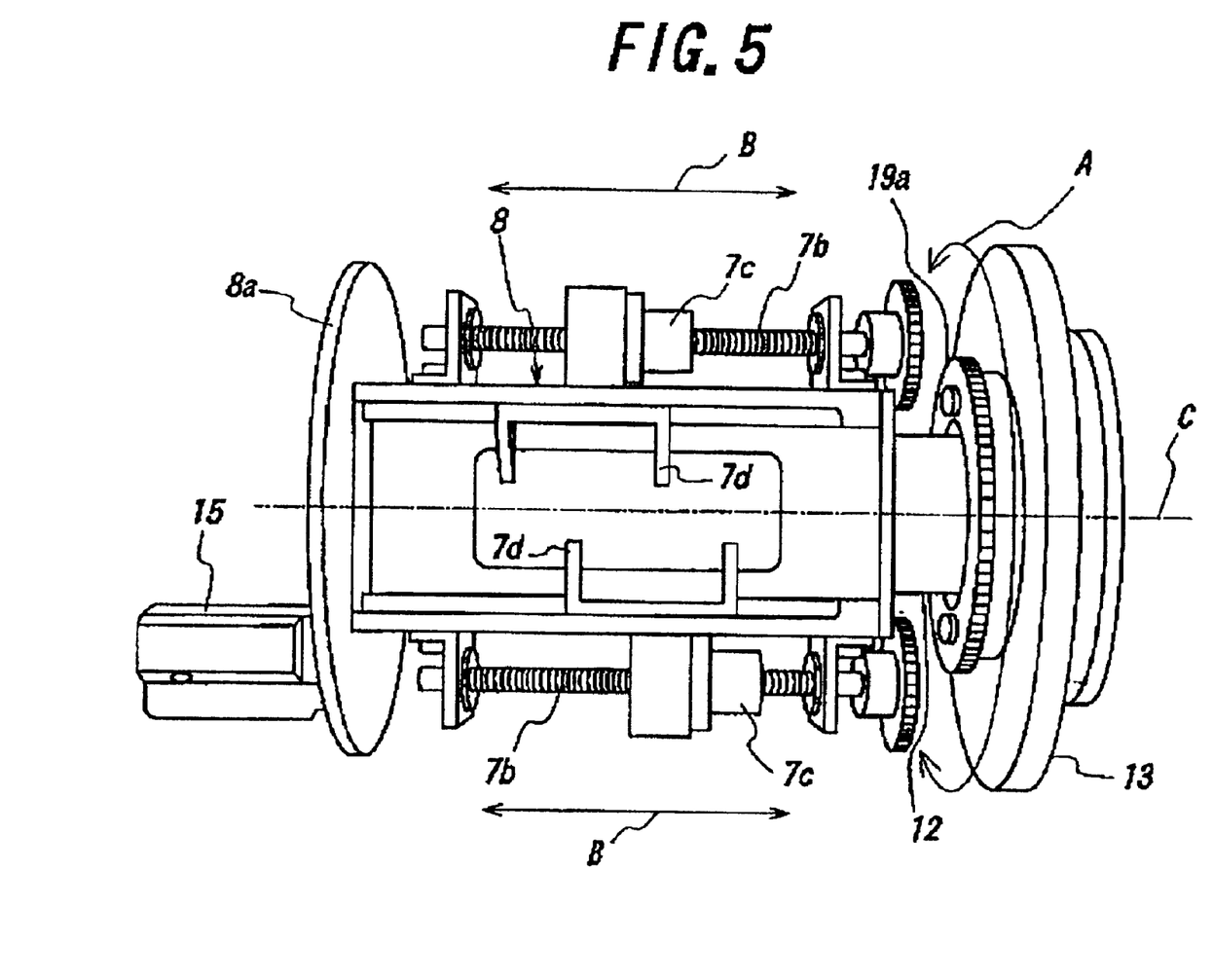
FIG. 5 is a partially exploded side view of a forceps bottom part of the active forceps of the above embodiment.

Further, the active forceps of this embodiment comprises a bottom part 9 having, as shown in FIGS. 2 and 5, three bottom side advancing and retreating members 6 each integrally coupled to the above three tip side advancing and retreating members 3 respectively via bar-like connecting members 5, while connected to one another relatively movable to the directions toward front and rear ends to constitute a link mechanism together with the above tip side advancing and retreating members 3 and the above tip supporting member 2, bottom frame 8 provided with a pair of linear actuators 7 as forward and backward actuating means for moving relatively to one another the bottom side advancing and retreating members 6 to the directions toward front and rear ends, and an annular flange plate 13 to support the bottom frame 8, via unillustrated bearing and hollow axis member 12, rotatably as shown by arrow A in FIG. 5 around axis C extending to the left and right in FIGS. 2 and 5. Then, the three bottom side advancing and retreating members 6 here are also fitted into one another, just like the three tip side advancing and retreating members 3 as shown in FIG. 4(*a*), slidable to the directions toward front and rear ends (to the left and right in FIG. 2), while, in an orthogonal direction thereto, coupled to one another relatively movable to the directions toward front and rear ends by inseparably engaging grooves and protrusions of hook-shaped cross section in this case.

The above three tip side advancing and retreating members 3 and three bottom side advancing and retreating members 6 here are respectively formed of high silicon stainless steel named silicolloy steel (trade name). This silicolloy steel is based on iron alloy with silicon (Si) contents of 3.5% or more, carbon contents of 0.02% or less, with nickel (Ni), manganese (Mn), chromium, etc. blended as needed to prevent embrittlement, excellent in properties that the conventional steel fail to achieve, such as toughness, heat resistance, corrosion resistance, abrasion resistance, high hardness, etc., while having an extremely small mutual friction coefficient of a little more than 0.1 i.e. about 50% of that of the conventional stainless steels such as SUS304, SUS316, etc. On the other hand, the forceps tip supporting member 2a and the ball 10 constituting a ball joint are formed of conventional stainless steel, since they slide very little.

Figure 6A:
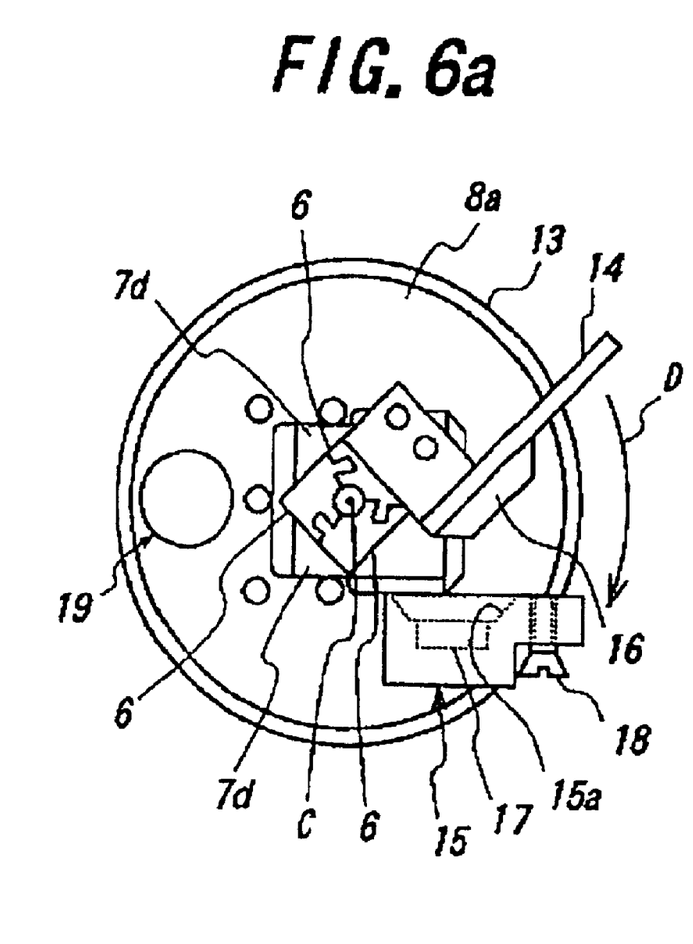
Figure 6B:
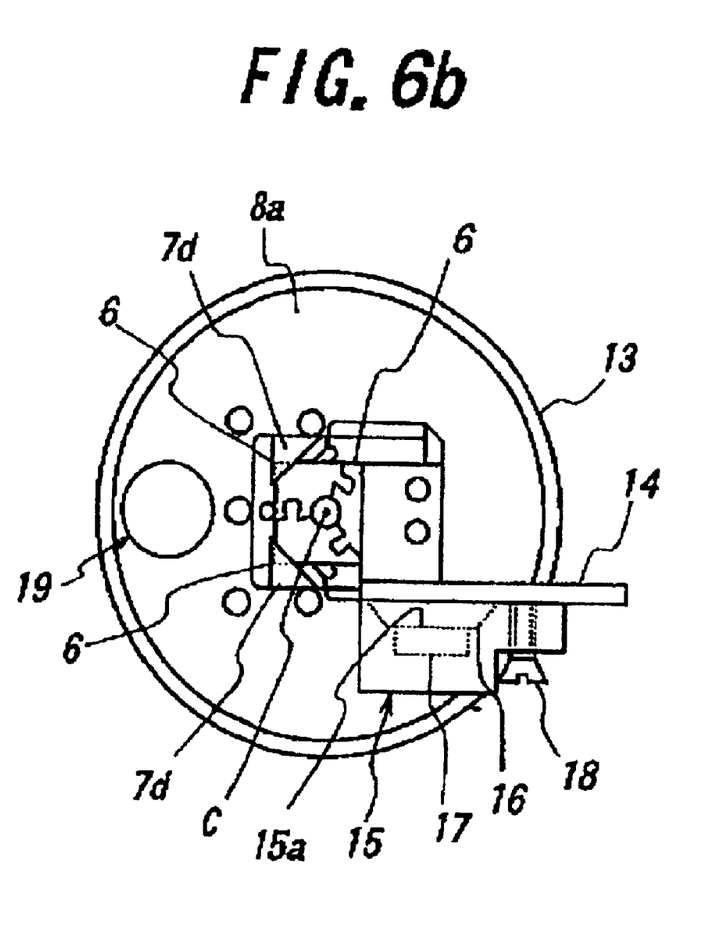

Then, in this embodiment, one of the above three bottom side advancing and retreating members 6 (the near side one in FIG. 2) is fixed at bottom frame 8 as shown in FIG. 6 as will be explained later, while the other two bottom side advancing and retreating members 6 are advanced or retreated by two linear actuators 7 to the directions toward front and rear ends as shown by arrow B in FIG. 5. The respective linear actuator 7 has a motor 7a (see FIG. 2) fixed on the side of bottom frame 8, ball screw axis 7b (see FIG. 5) rotatably supported also on the side of bottom frame 8 via a pair of L-shaped brackets and driven-coupled to the output axis of the motor 7a via a set of gear wheels, ball nut 7c secured with screws to the ball screw axis 7b, and U-shaped bracket 7d fixed at the ball nut 7c and arranged inside the bottom frame 8, while the above two bottom side advancing and retreating members 6 are respectively fitted to the U-shaped bracket 7d, as shown in FIG. 6.

In other words, the above three bottom side advancing and retreating members 6, composed with grooves of hook-shaped cross section and protrusions fitted into one another, are integrally coupled respectively via bar-like connecting member 5 to the above three tip side advancing and retreating members 3 similarly composed and assembled with forceps tip supporting member 2. Then, it is inserted into the bottom frame 8 through a central pore of circular rear end plate 8a fixed at the left end of the bottom frame 8 in FIG. 5. As shown in FIG. 6(a), it is inserted from the side of forceps tip supporting member 2 and tip side advancing and retreating members 3 at an inner end of U-shaped bracket 7d, which looks like a triangle in the same drawing, in a direction along an outer circumferential surface, which looks box-shaped in the same drawing. Those forceps tip supporting member 2, tip side advancing and retreating members 3 and connecting members 5 are inserted into the above hollow axis member 12 and a central pore of the annular flange plate 13. The most of those forceps tip supporting member 2, tip side advancing and retreating members 3 and connecting members 5 are projecting from the right side of flange plate 13 in FIG. 2. As shown by arrow D in FIG. 6(a), bracket 14 fixed at the above fixed bottom side advancing and retreating members 6, as backward projected from the rear end is rotated as a lever around axis C at an angle of approximately 45°. Thus, as shown in FIG. 6(b), the other two left bottom side advancing and retreating members 6 are fitted at corners into the pair of U-shaped bracket 7d.

Then, steel piece 16 fixed at bracket 14, which looks roughly like a reversed trapezoid in FIG. 6(a), is attracted by permanent magnet 17 in a magnet holder 15 fixed, as backward projected, at the above circular rear end plate 8a, the permanent magnet 17 being arranged at bottom of a recess 15a of the magnet holder 15, which looks like a reversed trapezoid in FIG. 6(a). Then, it is fitted into the recess 15a as shown in FIG. 6(b), thereby globally limiting rotation of three bottom side advancing and retreating members 6 around axis C relative to bottom frame 8 to prevent unintended departure of the above two bottom side advancing and retreating members 6 from a pair of U-shaped bracket 7d, while fixing the above fixed bottom side advancing and retreating members 6 relative to bottom frame 8. Thus equipped three bottom side advancing and retreating members 6 are removed from magnet holder 15 and from bottom frame 8 by rotating bracket 14 as a lever around axis C in a direction contrary to the above at an angle of approximately 45°, while the above two bottom side advancing and retreating members 6 also are removed from the pair of U-shaped brackets respectively and can be pulled out to the left in FIG. 2. Incidentally, magnet holder 15 is provided with a screw member 18 penetrated with threaded connection so as to push bracket 14 for the purpose of make it easy to remove the attracted steel piece 16 from permanent magnet 17 to allow rotation of the bracket 14.

Moreover, in this embodiment the above forceps bottom part 9 has a rotator 19 to rotate the bottom frame 8 around the above axis C parallel to the direction toward front and rear ends of the bottom side advancing and retreating members 6 together with two linear actuators 7 and three bottom side advancing and retreating members 6, and a cylindrical cover 20 (shown by cross section in FIG. 2) fixed at an end to the above annular flange plate 13 to cover the bottom frame 8, linear actuators 7, bottom side advancing and retreating members 6 and rotator 19. The rotator 19 here comprises an unillustrated pinion arranged at an output axis of an unillustrated motor with a built-in speed reducer fixed on the far side of bottom frame 8 in FIGS. 2 and 5, and an annular gear wheel 19a fixed on a face of the flange plate 13 directed to the bottom frame 8, engaged with each other. Thus, the bottom frame 8 is rotated, relative to the flange plate 13, by the working of the motor, together with the pair of linear actuators 7, three bottom side advancing and retreating members 6 and also the part toward the forceps tip 1 therefrom.

Incidentally, the active forceps in this embodiment are sized to design forceps bottom part 9 as small as possible i.e. 91 mm long excluding magnet holder 15, having an outer diameter of 73 mm, expecting it to be held by another robot, to have a distance of 290 mm between the rear end of bottom side advancing and retreating member 6 and the front end of tip side advancing and retreating member 3, assuming that the forceps tip 1 goes into a peritoneal cavity to a depth of about 150 mm, to have an outer diameter of 10 mm at the part from the bottom side advancing and retreating member 6 to the forceps tip 1, in accordance with Trocar's specification for the purpose of endoscopic use, allowing forceps tip 1 with an outer diameter of 1.5 mm to be fitted to the center section 2a of the forceps tip supporting member 2.

In the active forceps of such embodiment, two of the three bottom side advancing and retreating members 6 at the forceps bottom part 9 constituting link mechanisms together with the tip side advancing and retreating members 3 and the forceps tip supporting member 2 are fitted into the U-shaped bracket 7d of linear actuators 7. Then, either one or both of the two bottom side advancing and retreating members 6 are moved by one or both of the pair of linear actuators 7 arranged at the bottom frame 8 of the forceps bottom part 9, from the starting position as shown in FIG. 2, relatively to the bottom side advancing and retreating member 6 fixed at the bottom frame 8 or relatively to one another, to the directions toward front and rear ends. Then, three tip side advancing and retreating members 3 at the forceps tip part 4, integrally coupled to those bottom side advancing and retreating members 6 respectively via the connecting members 5, while connected to one another relatively movable to the directions toward front and rear ends, are relatively moved to the directions toward front and rear ends. As a result, one or two of the three arms 2b laterally projected from the center section 2a are moved toward front and rear ends of the tip side advancing and retreating members 3 by the forceps tip supporting member 2 at the forceps tip part 4 to oscillate as a whole around any of three axes making an angle of 120° between one another, thereby changing orientation of the forceps tip 1 supported at the center section 2a with 3 degrees of freedom.

Therefore, in the active forceps of this embodiment, the linear actuators 7 arranged at the bottom frame 8 constitute closed link mechanism together with the bottom side advancing and retreating members 6, the connecting members 5, the tip side advancing and retreating members 3 and the forceps tip supporting member 2 and can transmit a driving force to the forceps tip 1 to change orientation of the forceps tip 1. Therefore, a driving force is efficiently transmitted to the forceps tip 1, also giving higher stiffness to the forceps tip 1 than a wire-driven one, thereby enabling application of the active forceps to operations requiring a force at the forceps tip, such as evisceration. In addition, the tip side from the forceps bottom part 9, mainly provided only with the tip side advancing and retreating members 3, the forceps tip supporting member 2, the forceps tip 1 and connecting members 5, can be easily downsized with a smaller diameter than that of forceps bottom part 9, thereby enabling less invasive surgical operation also in requiring a strong force at forceps tip e.g. in the case of evisceration.

Moreover, in the active forceps of this embodiment, the forceps bottom part 9 has the rotator 19 to rotate the bottom frame 8 together with the linear actuators 7 and the bottom side advancing and retreating members 6 around axis C parallel to the directions of front and rear ends of the bottom side advancing and retreating members 6. Then, the rotator 19 rotates the bottom frame 8 together with the linear actuators 7, the bottom side advancing and retreating members 6 and also the part of tip side from the members 6 around the above axis C, thereby enabling the forceps tip 1 to pivot around the axis C. Therefore, the forceps tip 1 is highly stiffened, and the part nearer to the forceps tip 1 than the forceps bottom part 9 is downsized with a smaller diameter, while improving degrees of freedom in changing orientation of the forceps tip 1.

Moreover, in the active forceps of this embodiment, the three tip side advancing and retreating members 3 are fitted into one another slidably in the directions toward front and rear ends, while coupled to one another in an intersecting direction relatively movable in the directions toward front and rear ends by engaging grooves 3a and protrusions 3b. On the other hand, the three bottom side advancing and retreating members 6 are also fitted into one another slidably in the directions toward front and rear ends, while coupled to one another in an intersecting direction relatively movable in the directions toward front and rear ends by engaging grooves and protrusions. Then, the three tip side advancing and retreating members 3 and the three bottom side advancing and retreating members 6 are respectively coupled to one another with high stiffness, thereby highly stiffening the forceps tips 1 in a more simplified construction.

Moreover, in the active forceps of this embodiment, the three tip side advancing and retreating members 3 and the three bottom side advancing and retreating members 6 are respectively formed of silicolloy (trade name). In this case, a driving force can be transmitted more efficiently, through the affect of the extremely small friction coefficient between fellow silicolloy steel pieces.

Moreover, in the active forceps of this embodiment, the bottom frame 8 fixes with permanent magnet 17 one of the three bottom side advancing and retreating members 6, while the U-shaped brackets 7d of the pair of linear actuators 7 are removably fitted into the other two bottom side advancing and retreating members 6 to advance and retreating the bottom side advancing and retreating members 6. In this case, the bottom side advancing and retreating members 6 can be easily removed from the bottom frame 8 and the linear actuator 7 together with the part of forceps tip 1 side rather than the forceps bottom part 9, making it easy to change, wash, sterilize, etc. such part. In addition, one of the three bottom side advancing and retreating members 6 is fixed at the bottom frame 8, thereby enabling a smaller number of bottom side advancing and retreating members than the total number thereof to be directly moved, to downsize the forceps bottom part 9.

The present invention is not limited to the illustrated examples on which the above explanation is based, but may have four tip side advancing and retreating members 3 and four bottom side advancing and retreating members 6 respectively, optionally with four oscillating axes intersecting one another at right angles within a plane orthogonal to the above axis C. In that case, the bottom frame 8 may be provided therearound with four of the above linear actuators 7. On the other hand, provided that the forceps bottom part 9 has a rotator 19, a pair of tip side advancing and retreating members 3 and a pair of bottom side advancing and retreating members 6 may be arranged instead, while the above oscillating axis of forceps tip supporting member 2 may be one extending within a plane orthogonal to the above axis C. In that case, the bottom frame 8 may be provided on sides thereof with two of the above linear actuators 7 to actuate two bottom side advancing and retreating members 6.

Moreover, an active forceps of the present invention may be provided with an electric magnet, instead of the above permanent magnet 17, optionally using e.g. an electrically opening and closing solenoid forceps tips, instead of the above wire-driven forceps tip 1, or any other forceps tip having functions other than those of usual forceps tips, with different dimensions modified as needed.

What is claimed is:

1. An active forceps comprising:
   a forceps tip part having,
   a tip supporting member to support a forceps tip at a center section with a at least three arms laterally projected therefrom, and
   at least three tip side advancing and retreating members connected at a front end with said at least three arms respectively oscillatable while connected to one another relatively movable in directions toward front and rear ends; and
   a forceps bottom part having,
   at least three bottom side advancing and retreating members each integrally coupled to said at least three tip side advancing and retreating members, while connected to one another relatively movable in directions toward front and rear ends to constitute a link mechanism together with said at least three tip side advancing and retreating members and said tip supporting member, and
   a bottom frame provided with a forward and backward actuating means for moving relatively to one another said at least three bottom side advancing and retreating members in directions toward front and rear ends.

2. An active forceps as set forth in claim 1, wherein said forceps bottom part comprises a rotation actuating means to rotate said bottom frame around a predetermined axis parallel to said direction toward front and rear ends of said at least three bottom side advancing and retreating members together with said forward and backward actuating means and said at least three bottom side advancing and retreating members.

3. An active forceps as set forth in claim 1, wherein said at least three tip side advancing and retreating members and said at least three bottom side advancing and retreating members are slidably fitted into one another in directions toward front and rear ends, while, in an intersecting direction, coupled to one another relatively movable in directions toward front and rear ends by engaging grooves and protrusions.

4. An active forceps as set forth in claim 3, wherein at least either said at least three tip side advancing and retreating members or said at least three bottom side advancing and retreating members are formed of high-silicon stainless steel.

5. An active forceps as set forth in claim 1, wherein said forward and backward actuating means fix with magnet at said bottom frame one of said at least three bottom side advancing and retreating members, while removably fitting into the rest of said bottom side advancing and retreating members to advance or retreat said bottom side advancing and retreating members.

6. An active forceps as set forth in claim 2, wherein said at least three tip side advancing and retreating members and said at least three bottom side advancing and retreating members are slidably fitted into one another in directions toward front and rear ends, while, in an intersecting direction, coupled to one another relatively movable in directions toward front and rear ends by engaging grooves and protrusions.

7. An active forceps as set forth in any of claim 2, wherein said forward and backward actuating means fix with magnet at said bottom frame one of said at least three bottom side advancing and retreating members, while removably fitting into the rest of said bottom side advancing and retreating members to advance or retreat said bottom side advancing and retreating members.

8. An active forceps as set forth in any of claim 3, wherein said forward and backward actuating means fix with magnet at said bottom frame one of said at least three bottom side advancing and retreating members, while removably fitting into the rest of said bottom side advancing and retreating members to advance or retreat said bottom side advancing and retreating members.

9. An active forceps as set forth in any of claim 4, wherein said forward and backward actuating means fix with magnet at said bottom frame one of said at least three bottom side advancing and retreating members, while removably fitting into the rest of said bottom side advancing and retreating members to advance or retreat said bottom side advancing and retreating members.

* * * * *